(12) United States Patent
Ducray et al.

(10) Patent No.: US 7,485,751 B2
(45) Date of Patent: Feb. 3, 2009

(54) PROCESS FOR THE PREPARATION OF ENANTIOMERS OF AMIDOACETONITRILE COMPOUNDS FROM THEIR RACEMATES

(75) Inventors: Pierre Ducray, Village-Neuf (FR); Noelle Gauvry, Kembs-Loechle (FR); Thomas Goebel, Lorrach (DE); Francois Pautrat, Mulhouse (FR)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 11/667,148

(22) PCT Filed: Nov. 7, 2005

(86) PCT No.: PCT/EP2005/011884
§ 371 (c)(1),
(2), (4) Date: May 4, 2007

(87) PCT Pub. No.: WO2006/050887
PCT Pub. Date: May 18, 2006

(65) Prior Publication Data
US 2008/0045601 A1  Feb. 21, 2008

(30) Foreign Application Priority Data
Nov. 9, 2004 (EP) ................................. 04026510

(51) Int. Cl.
*C07C 231/00* (2006.01)
(52) U.S. Cl. ....................... 564/124; 514/622
(58) Field of Classification Search ............. 558/392; 564/124
See application file for complete search history.

(56) References Cited

U.S. PATENT DOCUMENTS

| 3,401,178 A | 9/1968 | Firestone et al. |
| 6,239,077 B1 * | 5/2001 | Andoh et al. ............... 504/312 |
| 2007/0072944 A1 | 3/2007 | Gauvry et al. |

* cited by examiner

*Primary Examiner*—Rei-Tsang Shiao
*Assistant Examiner*—Yong Chu

(74) *Attorney, Agent, or Firm*—Womble, Carlyle, Sandridge & Rice, PLLC

(57) ABSTRACT

The invention is directed at a new process for the preparation of pure enantiomers from the racemate of amidoacetonitrile compounds of formula

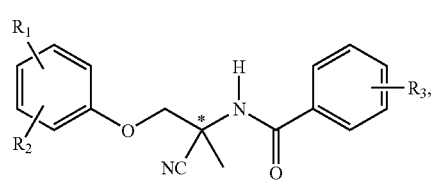

I wherein
$R_1$, $R_2$ and $R_3$, independently of each other, signify hydrogen, halogen, nitro, cyano, $C_1$-$C_6$-alkyl, halogen-$C_1$-$C_6$-alkyl, $C_1$-$C_6$-alkoxy, halogen-$C_1$-$C_6$-alkoxy, $C_2$-$C_6$-alkenyl, halogen-$C_2$-$C_6$-alkenyl, $C_2$-$C_6$-alkinyl, halogen-$C_2$-$C_6$-alkinyl, $C_2$-$C_6$-alkenyloxy, halogen-$C_2$-$C_6$-alkenyloxy, $C_1$-$C_6$-alkylthio, halogen-$C_1$-$C_6$-alkylthio, $C_1$-$C_6$-alkylsulfonyloxy, halogen-$C_1$-$C_6$-alkylsulfonyloxy, $C_1$-$C_6$-alkylsulfinyl, halogen-$C_1$-$C_6$-alkylsulfinyl, $C_1$-$C_6$-alkylsulfonyl, halogen-$C_1$-$C_6$-alkylsulfonyl, $C_1$-$C_6$-alkenylthio, halogen-$C_1$-$C_6$-alkenylthio, $C_1$-$C_6$-alkenylsulfinyl, halogen-$C_1$-$C_6$-alkenylsulfinyl, $C_1$-$C_6$-alkenylsulfonyl, halogen-$C_1$-$C_6$-alkenylsulfonyl, $C_1$-$C_6$-alkylamino, di-($C_1$-$C_6$-alkyl)amino, $C_1$-$C_6$-alkylaminocarbonyl, di-($C_1$-$C_6$-alkyl)aminocarbonyl, $C_1$-$C_6$-alkylsulfonylamino, halogen-$C_1$-$C_6$-alkylsulfonylamino, $C_1$-$C_6$-alkylcarbonyl, halogen-$C_1$-$C_6$-alkylcarbonyl, $C_1$-$C_6$-alkoxycarbonyl, unsubstituted or one- to five-fold substituted phenyl, unsubstituted or one- to five-fold substituted phenoxy, unsubstituted or one- to five-fold substituted phenylacetylenyl, unsubstituted or one- to four-fold substituted pyridyloxy, unsubstituted or one- to four-fold substituted pyridyl or unsubstituted or one- to seven-fold substituted naphthyl, the substituents in each case being selected from the group consisting of halogen, nitro, cyano, $C_1$-$C_6$-alkyl, halogen-$C_1$-$C_6$-alkyl, $C_1$-$C_6$-alkoxy and halogen-$C_1$-$C_6$-alkoxy,
which are useful in the control of endo- and ectoparasites in and on warm-blooded animals, especially productive livestock and domestic animals, as well as on plants.

29 Claims, No Drawings

PROCESS FOR THE PREPARATION OF ENANTIOMERS OF AMIDOACETONITRILE COMPOUNDS FROM THEIR RACEMATES

The present invention is directed at a new process for the preparation of pure enantiomers from the racemate of amidoacetonitrile compounds of formula

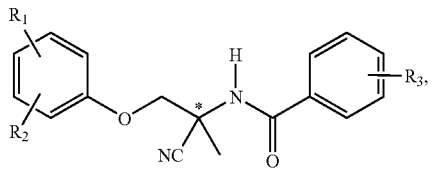

wherein
$R_1$, $R_2$ and $R_3$, independently of each other, signify hydrogen, halogen, nitro, cyano, $C_1$-$C_6$-alkyl, halogen-$C_1$-$C_6$-alkyl, $C_1$-$C_6$-alkoxy, halogen-$C_1$-$C_6$-alkoxy, $C_2$-$C_6$-alkenyl, halogen-$C_2$-$C_6$-alkenyl, $C_2$-$C_6$-alkinyl, halogen-$C_2$-$C_6$-alkinyl, $C_2$-$C_6$-alkenyloxy, halogen-$C_2$-$C_6$-alkenyloxy, $C_1$-$C_6$-alkylthio, halogen-$C_1$-$C_6$-alkylthio, $C_1$-$C_6$-alkylsulfonyloxy, halogen-$C_1$-$C_6$-alkylsulfonyloxy, $C_1$-$C_6$-alkylsulfinyl, halogen-$C_1$-$C_6$-alkylsulfinyl, $C_1$-$C_6$-alkylsulfonyl, halogen-$C_1$-$C_6$-alkylsulfonyl, $C_1$-$C_6$-alkenylthio, halogen-$C_1$-$C_6$-alkenylthio, $C_1$-$C_6$-alkenylsulfinyl, halogen-$C_1$-$C_6$-alkenylsulfinyl, $C_1$-$C_6$-alkenylsulfonyl, halogen-$C_1$-$C_6$-alkenylsulfonyl, $C_1$-$C_6$-alkylamino, di-($C_1$-$C_6$-alkyl)amino, $C_1$-$C_6$-alkylaminocarbonyl, di-($C_1$-$C_6$-alkyl)aminocarbonyl, $C_1$-$C_6$-alkylsulfonylamino, halogen-$C_1$-$C_6$-alkylsulfonylamino, $C_1$-$C_6$-alkylcarbonyl, halogen-$C_1$-$C_6$-alkylcarbonyl, $C_1$-$C_6$-alkoxycarbonyl, unsubstituted or one- to five-fold substituted phenyl, unsubstituted or one- to five-fold substituted phenoxy, unsubstituted or one- to five-fold substituted phenylacetylenyl, unsubstituted or one- to four-fold substituted pyridyloxy, unsubstituted or one- to four-fold substituted pyridyl or unsubstituted or one- to seven-fold substituted naphthyl, the substituents in each case being selected from the group consisting of halogen, nitro, cyano, $C_1$-$C_6$-alkyl, halogen-$C_1$-$C_6$-alkyl, $C_1$-$C_6$-alkoxy and halogen-$C_1$-$C_6$-alkoxy, which are useful in the control of endo- and ectoparasites in and on warm-blooded animals, especially productive livestock and domestic animals, as well as on plants.

Alkyl—as a group per se and as a structural element of other groups and compounds—is, in each case with due consideration of the specific number of carbon atoms in the group or compound in question, either straight-chained, i.e. methyl, ethyl, propyl, butyl, pentyl, hexyl, heptyl or octyl, or branched, e.g. isopropyl, isobutyl, sec.-butyl, tert.-butyl, isopentyl, neopentyl or isohexyl.

Alkenyl—as a group per se and as a structural element of other groups and compounds—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert.-pentenyl, isoheptenyl or isooctenyl.

Alkinyl—as a group per se and as a structural element of other groups and compounds—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Halogenalkoxy groups preferably have a chain length of 1 to 6 carbon atoms. Halogenalkoxy is e.g. fluoro-methoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy.

Halogen—as a group per se and as a structural component of other groups and compounds—is fluorine, chlorine, bromine or iodine, in particular fluorine, chlorine or bromine, especially fluorine or chlorine.

Halogen-substituted carbon-comprising groups and compounds can be partially halogenated or perhalogenated, it being possible, in the case of polyhalogenation, for the halogen substituents to be identical or different. Examples of halogenalkyl—as group per se and as a structural component of other groups and compounds—are methyl substituted up to three times by fluorine, chlorine and/or bromine, such as $CHF_2$ or $CF_3$; ethyl substituted up to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted up to seven times by fluorine, chlorine and/or bromine, such as $CH_2CHBrCH_2Br$, $CF_2CHFCF_3$, $CH_2CF_2CF_3$ or $CH(CF_3)_2$; butyl or one of its isomers substituted up to nine times by fluorine, chlorine and/or bromine, such as $CF(CF_3)CHFCF_3$ or $CH_2(CF_2)_2CF_3$; pentyl or one of its isomers substituted up to eleven times by fluorine, chlorine and/or bromine, such as $CF(CF_3)(CHF)_2CF_3$ or $CH_2(CF_2)_3CF_3$; and hexyl or one of its isomers substituted up to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Preferred embodiments within the scope of the invention are:

(1) The preparation of a pure enantiomer of a compound of formula I, wherein
$R_1$ and $R_2$, independently of each other, signify halogen, $C_1$-$C_6$halogenalkyl or CN;
in particular, independently of each other, $C_1$-$C_4$halogenalkyl or CN;
more particularly, independently of each other, halogenmethyl or CN;
most particularly, independently of each other, trifluoromethyl or CN;

(2) The preparation of a pure enantiomer of a compound of formula I, wherein
$R_3$ signifies halogen-$C_1$-$C_6$-alkoxy, halogen-$C_1$-$C_6$-alkylsulfonyl, halogen-$C_1$-$C_6$-alkylsulfinyl or halogen-$C_1$-$C_6$-alkylthio;
in particular halogen-$C_1$-$C_2$-alkoxy, halogen-$C_1$-$C_2$-alkylsulfonyl, halogen-$C_1$-$C_2$-alkylsulfinyl or halogen-$C_1$-$C_2$-alkylthio;
more particularly halogenmethoxy, halogenmethylsulfonyl, halogenmethylsulfinyl or halogenmethylthio;
most particularly trifluoromethoxy, trifluoromethylsulfonyl, trifluoromethylsulfinyl or trifluoromethylthio;

(3) The preparation of a pure enantiomer of a compound of formula I, wherein $R_1$ and $R_2$, independently of each other, signify halogen, $C_1$-$C_6$halogenalkyl or CN; and $R_3$ signifies halogen-$C_1$-$C_6$-alkoxy, halogen-$C_1$-$C_6$-alkylsulfonyl, halogen-$C_1$-$C_6$-alkylsulfinyl or halogen-$C_1$-$C_6$-alkylthio;

(4) The preparation of a pure enantiomer of a compound of formula I, wherein $R_1$ and $R_2$, independently of each other, signify $C_1$-$C_4$halogenalkyl or CN; and $R_3$ signifies halogen-$C_1$-$C_2$-alkoxy, halogen-$C_1$-$C_2$-alkylsulfonyl, halogen-$C_1$-$C_2$-alkylsulfinyl or halogen-$C_1$-$C_2$-alkylthio;

(5) The preparation of a pure enantiomer of a compound of formula I, wherein $R_1$ and $R_2$, independently of each other, signify halogenmethyl or CN; and $R_3$ signifies halogenmethoxy, halogenmethylsulfonyl, halogenmethylsulfinyl or halogenmethylthio;

(6) The preparation of a pure enantiomer of a compound of formula I, wherein $R_1$ and $R_2$, independently of each other, signify trifluoromethyl or CN; and $R_3$ signifies trifluoromethoxy, trifluoromethylsulfonyl, trifluoromethylsulfinyl or trifluoromethylthio.

The most preferred embodiment within the scope of the invention is the preparation of a pure enantiomer of N-(1-cyano-2-(5-cyano-2-trifluoromethyl-phenoxy)-1-methyl-ethyl)-4-trifluoromethylsulfanyl benzamide.

The synthesis of racemates of amidoacetonitrile compounds analogous to the one of formula I is well known and has been described in earlier publications, e.g. in EP 0 953 565 A2. Interestingly, it has been found that after separation of the racemates into the two pure enantiomers by standard methods, e.g. by chemical resolution using optically active acid or base or by chromatography on chiral adsorbents, e.g. high-pressure liquid chromatography on acetyl cellulose, one of them has proven to be biologically far less active (the distomer), whereas the other enantiomer is highly bioactive (the eutomer).

It goes without saying that for a large-scale production of parasiticides it is desirable to avoid the formation of any distomer during the synthesis of the compound, because these distomers not only result in a waste of starting material, but also "dilute" the bioactivity of the eutomer with the result of having to apply a higher amount of the parasiticides to achieve the same goal, sometimes even accompanied with undesirable side effects that would not occur with the pure eutomer. However, stereoselective syntheses are generally very expensive and, thus, not economical. Therefore, as an alternative, usually the eutomer is separated from the distomer and the latter simply discarded, by this means avoiding its dilutive and other side effects. Yet, evidently this alternative is not economical either. It would therefore be highly desirable to transform the distomer into the eutomer, preferably applying inexpensive means.

The present invention provides a solution to this requirement in that it is directed to the transformation of the distomer into the eutomer by simple and inexpensive means and subsequent isolation of the latter.

In order to achieve this goal, it is necessary to break one of the four bonds at the chiral carbon center and reform it from the opposite side. If the chiral carbon atom is neighbored by a heteroatom such as halogen, oxygen, nitrogen or sulfur, it is usually a carbon-heteroatom bond which is broken and reformed. Thus, a skilled person would expect that in the present case it is the bond between the starred chiral center in formula I and the nitrogen atom that is broken and reformed. In order to ease this carbon-nitrogen bond breaking mechanism a skilled person would add a Broensted or Lewis acid as a catalyst, which is known to weaken the carbon-nitrogen bond. Yet, it could be shown that the enantiomeric forms of the compounds of formula I are totally inert to acids with respect to a transformation or Racemization. In contrast to this observation, surprisingly, transformation of the distomer of formula I into a racemate of two enantiomeric forms proceeds very readily in the presence of a base and/or heating in polar solvents. This may be explained by the increased acidity of the hydrogen atom at the nitrogen of the amido group due to the strong mesomeric and inductive effect of the attached carbonyl function and the moderately inductive effect of the cyano group at the attached chiral substituent. Consequently, the Racemization mechanism is assumed to proceed as follows:

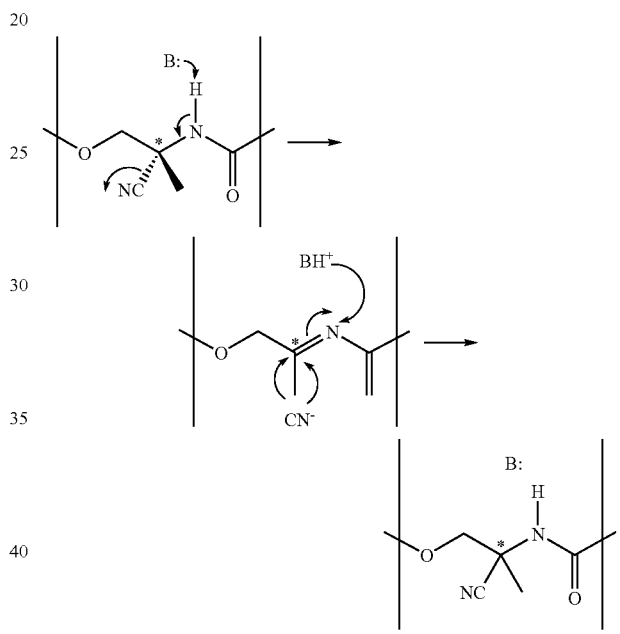

The present invention is therefore directed to a novel method of preparation of a single enantiomer from a racemate of compounds of formula I, characterized in that 1) the racemate is separated into two pure enantiomers by standard methods and the eutomer is collected, 2) the distomer is re-racemized using basic catalysis and/or heating in a polar solvent, and 3) the resulting racemate is again subjected to the separation procedure of step 1) in a repetitive cycle.

Hence, the invention is directed to the transformation of an distomeric form of a compound of formula I into the eutomer by a repetitive re-racemization—separation cycle.

The separation of the enantiomers is preferably carried out in a solvent or a mixture thereof. Mention may be made, as examples of such solvents or diluents, of aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloro-ethane, trichloroethene or tetrachloroethene; alcohols, such as methanol, ethanol, propanol, isopropanol, butanol, isobutanol or tert.

butanol; ethers, such as diethyl ether, dipropyl ether, diisopropyl ether, dibutyl ether, tert.-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphoramide; nitriles, such as acetonitrile or propionitrile; and sulfoxides, such as dimethyl sulfoxide. Preferred solvents are alcohols, in particular methanol, ethanol and mixtures thereof.

The separation of the enantiomers of the compounds of formula I is advantageously carried out by chromatography on chiral adsorbents using a Simulated Moving Bed (SMB) system. The SMB technique implies a countercurrent contact between the mobile phase carrying the enantiomers to be separated and the chiral stationary phase. An SMB unit is constituted of a number of chromatographic columns in a circular flow arrangement, separated by ports where inlet and outlet streams can be fed or collected. The countercurrent solid movement is simulated by periodically shifting the feed and withdrawal points of the unit in the same direction as the mobile flow. Four external streams are present:
a) the racemic feed mixture,
b) the desorbent, i.e. the eluent or the mixture of eluents constituting the mobile phase,
c) the extract stream enriched in the enantiomer A and
d) the raffinate stream enriched in the enantiomer B.

The streams divide the column unit into four sections:
1) section 1 between the desorbent inlet and the extract port,
2) section 2 between the extract port and the feed inlet,
3) section 3 between the feed inlet and the raffinate outlet, and
4) section 4 between the raffinate outlet and the desorbent inlet.

Each of these sections plays a specific role in the process. The separation is performed in section 2 and 3, where the less retained enantiomer B must be desorbed and carried by the mobile phase towards the raffinate outlet, whereas enantiomer A is retained by the stationary phase and carried towards the extract port through the simulated solid movement. In section 1, the stationary phase is regenerated by the feed of fresh desorbent, conveying enantiomer A towards the extract port. Finally, in section 4, the mobile phase is regenerated by the adsorption of enantiomer B not collected in the raffinate outlet. This way, both the stationary and the mobile phase can be recycled to section 4 and 1, respectively.

In the present invention, the stationary phase consists of a polysaccharide and the mobile phase is an alcohol, preferably methanol or ethanol, more preferably a mixture of methanol and alcohol, in particular a 1:1-mixture of methanol and alcohol.

The invention especially relates to the separation-re-racemization cycle described in the example.

The re-racemization of the distomer is preferably carried out in a solvent or a mixture thereof. Mention may be made, as examples of such solvents or diluents, of aromatic, heteroaromatic, aliphatic and alicyclic hydrocarbons and halogenated hydrocarbons, such as benzene, toluene, xylene, mesitylene, tetralin, chlorobenzene, dichlorobenzene, bromobenzene, pyridine, petroleum ether, hexane, cyclohexane, dichloromethane, trichloromethane, tetrachloromethane, dichloroethane, trichloroethene or tetrachloroethene; alcohols, such as methanol, ethanol, propanol, isopropanol, butanol, isobutanol or tert. butanol; ethers, such as diethyl ether, dipropyl ether, diisopropyl ether, dibutyl ether, tert.-butyl methyl ether, ethylene glycol monomethyl ether, ethylene glycol monoethyl ether, ethylene glycol dimethyl ether, dimethoxydiethyl ether, tetrahydrofuran or dioxane; esters, such as methyl acetate, ethyl acetate or tert.-butyl acetate; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphoramide; nitriles, such as acetonitrile or propionitrile; and sulfoxides, such as dimethyl sulfoxide. Preferred solvents are ethers, in particular tetrahydrofuran or dioxane, most preferred dioxane.

Suitable bases for facilitating the re-racemization reaction are e.g. alkali metal or alkaline earth metal hydroxides, hydrides, amides, alkanolates, acetates, carbonates, cyanides, dialkylamides or alkylsilylamides; alkylamines, alkylenediamines, optionally N-alkylated, optionally unsaturated, cycloalkylamines, basic heterocycles, ammonium hydroxides, as well as carbocyclic amines. Those which may be mentioned by way of example are sodium hydroxide, hydride, amide, methanolate, acetate, carbonate, cyanide, potassium tert.-butanolate, hydroxide, carbonate, hydride, lithium diisopropylamide, potassium bis(trimethyl-silyl)-amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU). Particularly preferred bases are sodium cyanide, sodium bicarbonate, sodium carbonate, sodium hydride, potassium carbonate or potassium tert.-butanolate. Most preferred is sodium cyanide.

The reaction advantageously takes place in a temperature range of ca. 20° C. to ca. 150° C., preferably from ca. 80° C. to ca. 120° C.

In a preferred embodiment, an enantiomer of formula I is re-racemized in a temperature range of about 80° C. to about 120° C., preferably at about 101° C., in an ether, preferably 1,4-dioxane, preferably in the presence of sodium cyanide.

PREPARATION EXAMPLES a) Separation of Enantiomers of N-(1-cyano-2-(5-cyano-2-trifluoromethyl-phenoxy)-1-methyl-ethyl)-4-trifluoromethylsulfanyl benzamide A feed solution of 4.146 kg of the title compound in 62.22 lt of a 1:1-ethanol/methanol mixture is prepared and stirred under nitrogen until complete dissolution is achieved. This solution is then filtered through an inline filter into a glass vessel which is connected to a Simulated Moving Bed (SMB) system (Novasep Licosep Lab unit) and filled up with a 1:1-ethanol/methanol mixture to a total volume of 120 lt. The feed solution is then continuously injected into the SMB system, which is equipped with eight identical columns of 10.0 cm length, 4.8 cm internal diameter and containing 110 g of a Chiralpak polysaccharide as a stationary phase each in a 2-2-2-2 configuration, and the enantiomers separated using a 1:1-ethanol/methanol mixture as the mobile phase. The target eutomer is extracted from the stream. The chiral purity of the eutomer ((−)-(S)-N-(1-cyano-2-(5-cyano-2-trifluoromethyl-phenoxy)-1-methyl-ethyl)-4-trifluoromethylsulfanyl benzamide is 99.65% with a melting point of 126-7° C. and an optical rotational angle of −37.8° at a concentration of 20.9 mmol/lt in methylene chloride.

The distomeric form is re-racemized according to the procedure described in the following.

b) Racemization of (+)-(R)-N-(1-cyano-2-(5-cyano-2-trifluoromethyl-phenoxy)-1-methyl-ethyl)-4-trifluoromethylsulfanyl benzamide In 3.4 lt of 1,4-dioxane, a mixture of 500 g of (+)-(R)-N-(1-cyano-2-(5-cyano-2-trifluoro-methyl-phenoxy)-1-methyl-ethyl)-4-trifluoromethylsulfanyl benzamide and 43.48 g of sodium cyanide are stirred for 7 to 9 h at an internal temperature of 101° C. Then about 60-70% of the solvent is distilled off at 45° C. and a pressure of 140 mbar and the oily residue diluted with 3 lt of isopropyl acetate, followed by a semi-saturated aqueous solution of sodium chloride. After stirring the resulting emulsion at 40° C. for 15 min, the organic layer is separated, washed with a semi-saturated aqueous solution of sodium chloride and concentrated by distilling off about 15% of its volume. After addition of 3 lt of methylcyclohexane the homogeneous mixture is left to cool to 20° C. within 4-5 h and then chilled to 0° C. within 2 h. The precipitating suspension is then filtered and the filter residue washed with methylcyclohexane and finally dried to afford the racemic form of title compound. The racemate thus obtained is then again subjected to the separation procedure described above.

This separation-re-racemization cycle is generally applicable to all the compounds of formula I.

What is claimed:

1. A method of preparation of a single enantiomer from the racemate of an amidoacetonitrile compound of formula

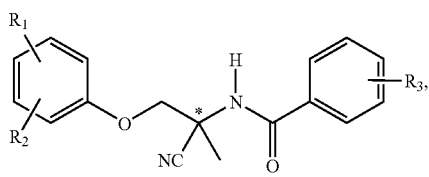

wherein
$R_1$, $R_2$ and $R_3$, independently of each other, signify hydrogen, halogen, nitro, cyano, $C_1$-$C_6$-alkyl, halogen-$C_1$-$C_6$-alkyl, $C_1$-$C_6$-alkoxy, halogen-$C_1$-$C_6$-alkoxy, $C_2$-$C_6$-alkenyl, halogen-$C_2$-$C_6$-alkenyl, $C_2$-$C_6$-alkinyl, halogen-$C_2$-$C_6$-alkinyl, $C_2$-$C_6$-alkenyloxy, halogen-$C_2$-$C_6$-alkenyloxy, $C_1$-$C_6$-alkylthio, halogen-$C_1$-$C_6$-alkylthio, $C_1$-$C_6$-alkylsulfonyloxy, halogen-$C_1$-$C_6$-alkylsulfonyloxy, $C_1$-$C_6$-alkylsulfinyl, halogen-$C_1$-$C_6$-alkylsulfinyl, $C_1$-$C_6$-alkylsulfonyl, halogen-$C_1$-$C_6$-alkylsulfonyl, $C_1$-$C_6$-alkenylthio, halogen-$C_1$-$C_6$-alkenylthio, $C_1$-$C_6$-alkenylsulfinyl, halogen-$C_1$-$C_6$-alkenylsulfinyl, $C_1$-$C_6$-alkenylsulfonyl, halogen-$C_1$-$C_6$-alkenylsulfonyl, $C_1$-$C_6$-alkylamino, di-($C_1$-$C_6$-alkyl)amino, $C_1$-$C_6$-alkylaminocarbonyl, di-($C_1$-$C_6$-alkyl)aminocarbonyl, $C_1$-$C_6$-alkylsulfonylamino, halogen-$C_1$-$C_6$-alkylsulfonylamino, $C_1$-$C_6$-alkylcarbonyl, halogen-$C_1$-$C_6$-alkylcarbonyl, $C_1$-$C_6$-alkoxycarbonyl, unsubstituted or one- to five-fold substituted phenyl, unsubstituted or one- to five-fold substituted phenoxy, unsubstituted or one- to five-fold substituted phenylacetylenyl, unsubstituted or one- to four-fold substituted pyridyloxy, unsubstituted or one- to four-fold substituted pyridyl or unsubstituted or one- to seven-fold substituted naphthyl, the substituents in each case being selected from the group consisting of halogen, nitro, cyano, $C_1$-$C_6$-alkyl, halogen-$C_1$-$C_6$-alkyl, $C_1$-$C_6$-alkoxy and halogen-$C_1$-$C_6$-alkoxy, characterized in that
1) the racemate is separated into two pure enantiomers by standard methods and the eutomer is collected,
2) the distomer is re-racemized using basic catalysis and/or heating in a polar solvent, and
3) the resulting racemate is again subjected to the separation procedure of step 1) in a repetitive cycle.

2. A method of preparation of a single enantiomer from the racemate of a compound of formula I according to claim 1, wherein $R_1$ and $R_2$, independently of each other, signify halogen, $C_1$-$C_6$halogenalkyl or CN.

3. A method of preparation of a single enantiomer from the racemate of a compound of formula I according to claim 1, wherein $R_1$ and $R_2$, independently of each other, signify $C_1$-$C_4$halogenalkyl or CN.

4. A method of preparation of a single enantiomer from the racemate of a compound of formula I according to claim 1, wherein $R_1$ and $R_2$, independently of each other, signify halogenmethyl or CN.

5. A method of preparation of a single enantiomer from the racemate of a compound of formula I according to claim 1, wherein $R_1$ and $R_2$, independently of each other, signify trifluoromethyl or CN.

6. A method of preparation of a single enantiomer from the racemate of a compound of formula I according to claim 1, wherein $R_3$ signifies halogen-$C_1$-$C_6$-alkoxy, halogen-$C_1$-$C_6$-alkylsulfonyl, halogen-$C_1$-$C_6$-alkylsulfinyl or halogen-$C_1$-$C_6$-alkylthio.

7. A method of preparation of a single enantiomer from the racemate of a compound of formula I according to claim 1, wherein $R_3$ signifies halogen-$C_1$-$C_2$-alkoxy, halogen-$C_1$-$C_2$-alkylsulfonyl, halogen-$C_1$-$C_2$-alkylsulfinyl or halogen-$C_1$-$C_2$-alkylthio.

8. A method of preparation of a single enantiomer from the racemate of a compound of formula I according to claim 1, wherein $R_3$ signifies halogenmethoxy, halogenmethylsulfonyl, halogenmethylsulfinyl or halogenmethylthio.

9. A method of preparation of a single enantiomer from the racemate of a compound of formula I according to claim 1, wherein $R_3$ signifies trifluoromethoxy, trifluoromethylsulfonyl, trifluoromethylsulfinyl or trifluoromethylthio.

10. A method of preparation of a single enantiomer from the racemate of a compound of formula I according to claim 1, wherein $R_1$ and $R_2$, independently of each other, signify halogen, $C_1$-$C_6$halogenalkyl or CN; and $R_3$ signifies halogen-$C_1$-$C_6$-alkoxy, halogen-$C_1$-$C_6$-alkylsulfonyl, halogen-$C_1$-$C_6$-alkylsulfinyl or halogen-$C_1$-$C_6$-alkylthio.

11. A method of preparation of a single enantiomer from the racemate of a compound of formula I according to claim 1, wherein $R_1$ and $R_2$, independently of each other, signify $C_1$-$C_4$halogenalkyl or CN; and $R_3$ signifies halogen-$C_1$-$C_2$-alkoxy, halogen-$C_1$-$C_2$-alkylsulfonyl, halogen-$C_1$-$C_2$-alkylsulfinyl or halogen-$C_1$-$C_2$-alkylthio.

12. A method of preparation of a single enantiomer from the racemate of a compound of formula I according to claim 1, wherein $R_1$ and $R_2$, independently of each other, signify halogenmethyl or CN; and $R_3$ signifies halogenmethoxy, halogenmethylsulfonyl, halogenmethylsulfinyl or halogenmethylthio.

13. A method of preparation of a single enantiomer from the racemate of a compound of formula I according to claim 1, wherein $R_1$ and $R_2$, independently of each other, signify trifluoromethyl or CN; and $R_3$ signifies trifluoromethoxy, trifluoromethylsulfonyl, trifluoromethylsulfinyl or trifluoromethylthio.

14. A method of preparation of a single enantiomer from the racemate of N-(1-cyano-2-(5-cyano-2-trifluoromethyl-phenoxy)-1-methyl-ethyl)-4-trifluoromethylsulfanyl benzamide according to claim 1.

15. A method of preparation of a single enantiomer from the racemate of a compound of formula I according to claim 1, characterized in that the separation of the enantiomers is carried out by chromatography on a chiral adsorbent.

16. A method of preparation of a single enantiomer from the racemate of a compound of formula I according to claim 1, characterized in that the chromatographical separation is carried out on a chiral polysaccharide as the stationary phase with an alcohol as the mobile phase.

17. A method of preparation of a single enantiomer from the racemate of a compound of formula I according to claim 1, characterized in that the chromatographical separation is carried out with a mixture of methanol and alcohol as the mobile phase.

18. A method of preparation of a single enantiomer from the racemate of a compound of formula I according to claim 1, characterized in that the re-racemization reaction of the distomer is carried out in an ether.

19. A method of preparation of a single enantiomer from the racemate of a compound of formula I according to claim 1 characterized in that the re-racemization reaction of the distomer is carried out in tetrahydrofuran or dioxane.

20. A method of preparation of a single enantiomer from the racemate of a compound of formula I according to claim 1, characterized in that the re-racemization reaction of the distomer is carried out in dioxane.

21. A method of preparation of a single enantiomer from the racemate of a compound of formula I according to claim 1, characterized in that the re-racemization reaction of the distomer is carried out in the presence of sodium cyanide, sodium bicarbonate, sodium carbonate, sodium hydride, potassium carbonate or potassium tert.-butanolate.

22. A method of preparation of a single enantiomer from the racemate of a compound of formula I according to claim 1, characterized in that the re-racemization reaction of the distomer is carried out in the presence of sodium cyanide.

23. A method of preparation of a single enantiomer from the racemate of a compound of formula I according to claim 1, characterized in that the re-racemization reaction of the distomer is carried out in a temperature range of about 80° C. to about 120° C.

24. A method of preparation of a single enantiomer from the racemate of a compound of formula I according to claim 1, characterized in that the re-racemization reaction of the distomer is carried out at about 101° C.

25. A method of preparation of a single enantiomer from the racemate of a compound of formula I according to claim 1, characterized in that the separation of the enantiomers is carried out by chromatography on a chiral adsorbent and the re-racemization reaction of the distomer is carried out in an ether and in the presence of sodium cyanide, sodium bicarbonate, sodium carbonate, sodium hydride, potassium carbonate or potassium tert.-butanolate in a temperature range of about 80° C. to about 120° C.

26. A method of preparation of a single enantiomer from the racemate of a compound of formula I according to claim 1, characterized in that the chromatographical separation is carried out on a chiral polysaccharide as the stationary phase with an alcohol as the mobile phase and the re-racemization reaction of the distomer is carried out in tetrahydrofuran or dioxane and in the presence of sodium cyanide at about 101° C.

27. A method of preparation of a single enantiomer from the racemate of a compound of formula I according to claim 1, characterized in that the chromatographical separation is carried out on a chiral polysaccharide as the stationary phase with a mixture of methanol and alcohol as the mobile phase and the re-racemization reaction of the distomer is carried out in dioxane and in the presence of sodium cyanide at about 101° C.

28. A method of preparation of a single enantiomer from the racemate of N-(1-cyano-2-(5-cyano-2-trifluoromethyl-phenoxy)-1-methyl-ethyl)-4-trifluoromethylsulfanyl benzamide according to claim 14, characterized in that the chromatographical separation is carried out on a chiral polysaccharide as the stationary phase with a mixture of methanol and alcohol as the mobile phase and the re-racemization reaction of the distomer is carried out in dioxane and in the presence of sodium cyanide at about 101° C.

29. A method of preparation of (−)-(R)-N-(1-cyano-2-(5-cyano-2-trifluoromethyl-phenoxy)-1-methyl-ethyl)-4-trifluoromethylsulfanyl benzamide from the racemate according to claim 28.

* * * * *